United States Patent [19]

Pedersen et al.

[11] Patent Number: 4,572,833
[45] Date of Patent: Feb. 25, 1986

[54] METHOD FOR PREPARING A PHARMACEUTICAL CONTROLLED RELEASE COMPOSITION

[75] Inventors: Arne M. Pedersen, Vanløse; Jens R. Jensen, Stenlose, both of Denmark

[73] Assignee: A/S Alfred Benzon, Copenhagen, Denmark

[21] Appl. No.: 523,636

[22] Filed: Aug. 15, 1983

[30] Foreign Application Priority Data

Aug. 13, 1982 [DK] Denmark .............................. 3653/82

[51] Int. Cl.[4] .......................... A61K 9/22; A61K 9/48; A61K 9/50; A61K 9/54
[52] U.S. Cl. ......................................... 424/20; 424/22; 424/31; 424/32; 424/33; 424/34; 424/35; 424/36; 424/37; 424/38; 424/153; 427/3
[58] Field of Search .................................. 424/31–38, 424/125, 153, 20, 22; 427/3

[56] References Cited

U.S. PATENT DOCUMENTS

| | | | |
|---|---|---|---|
| 2,940,901 | 6/1960 | Hiatt et al. | 424/153 |
| 3,909,444 | 9/1975 | Anderson et al. | 427/3 |
| 4,173,626 | 11/1979 | Dempski et al. | 424/19 |
| 4,193,985 | 3/1980 | Pedersen . | |
| 4,259,315 | 3/1981 | Lippmann et al. | 424/153 |
| 4,267,138 | 5/1981 | Dobo et al. | 427/3 |
| 4,302,440 | 11/1981 | John et al. | 427/3 |
| 4,316,884 | 2/1982 | Alam et al. | 424/19 |
| 4,322,449 | 3/1982 | Voss et al. | 424/3 |
| 4,353,887 | 10/1982 | Hess et al. | 424/19 |
| 4,359,483 | 11/1982 | Kaetsu et al. | 424/3 |
| 4,411,933 | 10/1983 | Samejima et al. | 424/19 |

FOREIGN PATENT DOCUMENTS 0013262 12/1979 European Pat. Off. .
1468172 3/1977 United Kingdom .

OTHER PUBLICATIONS

Baggesen et al.–"Content and Dissolution Uniformity Testing of Controlled Release Products–The Repro–Dose Quality Control Procedure"; 1981.

Bechegaard & Nielsen; "Controlled-Release Multiple-Units and Single-Unit Doses"; 1978.
Bechgaard and Ladesfoged; "Distribution of Pellets in the Gastrointestinal Tract. The Influence on Transit Time Exerted by the Density or Diameter of Pellets"; Aug. 8, 1978.
Bechgaard and Baggesen; "Propoxyphene and Norpropoxyphene Influence of Type of Controlled-Release Formulation on Intra- and Intersubject Variations"; Nov. 1980.
D. M. Green, M.D.; "Tablets of Coated Aspirin Microspherules——A New Dosage Form"; Sep.–Oct., 1966.

(List continued on next page.)

Primary Examiner—Ronald W. Griffin
Attorney, Agent, or Firm—Stiefel, Gross, Kurland & Pavane

[57] ABSTRACT

A pharmaceutical oral multiple-units composition with controlled release, in which the individual units are coated units of an active substance, e.g. potassium chloride, which is subject to controlled release in consequence of the units being coated with a substantially water-insoluble, but with a water-diffusable coating, is prepared by applying on units comprising the active substance, a film-forming coating mixture comprising a solvent, a film-forming substance dissolved in the solvent and a hydrophobic substance, such as a wax, e.g. a paraffin wax, the film coating mixture being applied at a temperature higher than the melting point of the hydrophobic substance. The application is preferably performed in a fluidized bed.

By thus incorporating a hydrophobic substance in the coating mixture in an amount of the order 1–25% in such a way that prior to the application, the hydrophobic substance is melted, but undissolved and microdispersed in the coating mixture, a coating is obtained which delays and controls the diffusion through the coating so that even easily soluble active substances, such as potassium chloride, can be slowly released.

20 Claims, 3 Drawing Figures

OTHER PUBLICATIONS

McDonald et al.; "Studies on Absorption of a Newly Developed Enteric-Coated Erythromycin Base"; Oct. 1977.

W. M. Cochran; "Statistical Methods-Applied to Experiments in Agriculture and Biology".

Bogentoft et al.; "Influence of Food on the Absorption of Acetylsalicylic Acid from Enteric-Coated Dosage Forms"; 1978.

Bechgaard, H., Hegermann Nielsen, G. & Aggerbeck, A. (1979) Kalinorm. En polydepot tablet med kontrolleret udlosning af kaliumklorid. *In vitro* og *in vivo* dokumentation. Farm. Tid. 89; 761–766.

Ben-Ishay, D. Englemann, K. (1979) Bioavailability of Potassium from a Slow-Release Tablet, Clin. Pharmacol. Ther. 14: 250–258.

Stoutakis, V. A., acchiardo, S. R. acchiardo, A. S. and A. B. Feigenbaum (1979), Bioavailability of Potassium from a Slow-Release Tablet, Curr. Ther. Res. 15: 104–112.

Tannen, R. L., Cordano, A. (1978) Pharmakokinetics and Effects on Fecal Blood Loss of a Controlled Release Potassium Chloride Tablet, J. Pharmacol. Ex. Ther.: 240–246.

Brophy, M. R. & Deasy, P. B., Influence of Coating and Core Modifications on the in vitro Release of Methylene Blue from Ethylcellulose Microcapsules Produced by Pan Coating Procedure, J. Pharm. Pharmacol, 33 (1981), pp. 495–499.

Harris, M. S., Preparation and Release Characteristics of Potassium Chloride Microcapsules, J. Pharm, 70 (1981) 391–394.

METHOD FOR PREPARING A PHARMACEUTICAL CONTROLLED RELEASE COMPOSITION

The present invention relates to an oral pharmaceutical controlled release multiple-units dosage form with important new features.

TECHNICAL BACKGROUND

Many physiological factors influence both the gastrointestinal transit time and the release of a drug from a controlled release dosage form and thus the uptake of the drug into the systemic circulation. Dosage forms should therefore be designed so that such variable factors do not compromise the efficacy and safety of the product.

In humans, a reproducible gastrointestinal transit time of a depot formulation can be achieved only by a controlled release multiple-units dosage form.

The term "controlled release multiple-units formulation" (Bechgaard & Hegermann Nielsen, 1978) indicates a pharmaceutical formulation comprising a multiplicity (typically at least 100) of individual coated (or "micro-encapsulated") units contained in the formulation in such a form that the individual units will be made available from the formulation upon disintegration of the formulation in the stomach of animals, including humans, who have ingested the formulation. Typically, the multiple-units formulation may be a capsule which disintegrates in the stomach to make available a multiplicity of individual coated units contained in the capsule, or a tablet which disintegrates in the stomach to make available a multiplicity of coated units originally combined in the tablet.

Drug release from a controlled release dosage form is generally controlled either by diffusion through a coating or by erosion of a coating by a process dependent on, e.g., enzymes or pH. The importance of a pH independent diffusion with respect to obtaining a reproducible rate of availability and to minimizing intra- and intersubject variations is known (GB Pat. No. 1 468 172 and Bechgaard & Baggesen, 1980). It is also known that controlled drug release in vivo can be achieved through an erodable process by enteric coating of a multiple-units dosage form (Green, 1966; McDonald et al., 1977; Bogentoft et al., 1978).

Both above-mentioned types of controlled release multiple-units formulation techniques aim at a controlled release of active substance in a predetermined pattern to reduce and delay the peak plasma concentration without affecting the extent of drug availability. Due to a lower peak plasma concentration, the frequency of undesirable side-effects may be reduced, and due to the delay in the time it takes to obtain the peak plasma concentration and the prolongation of the time at the therapeutically active plasma concentration, the dosage frequency may be reduced to a dosage taken only twice or once daily, in order to improve patient compliance.

A further advantage of the controlled release multiple-units dosage form is that high local concentrations of the active substance in the gastrointestinal system is avoided, due to the units being distributed freely throughout the gastrointestinal tract, independent of gastric emptying. If the mucosa of the stomach is more sensitive to the active substance than the intestinal mucosa, controlled release formulations avoiding release of active substance in the gastric area will be preferred; formulations of this type are controlled release multiple-units formulations in which the coatings are substantially resistant to gastric conditions.

The present invention deals with multiple-units dosage forms which are diffusion-coated.

In the known art preparation of diffusion-coated controlled release multiple-units formulations, diffusion film-coating mixtures have been used which contain synthetic film-forming agents dissolved or dispersed in organic solvents, e.g. isopropanol, ethanol, acetone, or mixtures thereof. However, in particular when the units contain a readily soluble active substance, it has been difficult to obtain a sufficiently slow release of the active substance.

DISCLOSURE OF INVENTION

The present invention provides a method for preparing a pharmaceutical oral controlled release multiple-units formulation in which individual units comprise coated units of an active substance which is subject to controlled release as a result of coating the units with a substantially water-insoluble, but water-diffusable controlled release coating, characterized in that the units are coated with a coating mixture comprising a solvent, a film-forming polymeric substance, a plasticizer, and a hydrophobic substance which by itself is capable of forming a continuous phase, the coating being performed by applying the coating mixture on the units in a fluidized bed at a temperature above the melting temperature of the hydrophobic substance.

It is known from the literature (Brophy & Deasy, 1981) that units coated with a diffusion-coating can be made to release their content of active substance over a longer period of time by incorporation of a hydrophobic agent such as paraffin wax in a coating solution. However, the same reference states that the measure is not satisfactory as a means of prolonging drug release.

As appears from the experimental data given in the examples, it has surprisingly been found that addition of a hydrophobic substance to a coating mixture containing a film-forming polymeric substance and application of the coating mixture under the conditions stated above will result in a coating which delays and controls the diffusion through a coating of the polymer film in a useful and reproducible manner to confer desirable controlled release characteristics to the coated units. Thereby, film forming polymers which in themselves are diffusion-controlling to an insufficient extent are improved to obtain a more efficient diffusion control.

The present invention is of particular importance in connection with the coating of substances which exert a local irritating effect on the mucosa of the gastrointestinal tract such as potassium chloride, non-steroidal anti-inflammatory drugs, e.g. acetylsalicylic acid, propionic acid derivatives such as ibuprofene, lithium salts, and ferrous salts, because a prolonged period of release from multiple-units will on the one hand secure a minimized risk of local high concentration of the active substance due to the distribution of the units and on the other hand permit a generally lower concentration. For instance, potassium chloride microcapsules should ideally be released over a prolonged period of at least four hours in a reference in vitro dissolution system. From Harris (1981), it is known to film-coat potassium chloride crystals with a diffusion membrane (acacia and gelatin) after various pre-treatments of the crystals to protect them from the aqueous environment present during the microencapsulation process. One of the mixtures used for precoating of the crystals comprises hydroxypropyl methylcellulose and wax, and another system comprises hydroxypropyl methylcellulose plus a wax coating. In all cases, however, the release of potassium chloride in the in vitro systems is very fast, of the order of a few minutes.

According to the present invention, a slow release of even readily soluble active substances such as potassium chloride may be obtained, such as appears from the examples.

The film-coating mixture is prepared and applied under such conditions that the hydrophobic substance must be considered to be effectively microdispersed in fluid condition throughout the coating solution.

Compared with pan-coating from a solution (in toluene) as known from Brophy & Deasy (1981), the method of the invention in which the film coating mixture is applied in a state where the hydrophobic constituent is in an undissolved, but microdispersed state, the prolonged controlled release obtained according to the present invention is presumed to be due to the manner in which the hydrophobic agent distributes itself under the prevailing evaporation conditions. It is presumed that the controlled evaporation conditions during the fluid bed application, combined with the fact that the hydrophobic substance is in a molten, but undissolved and microdispersed state results in a more uniform distribution of the hydrophobic substance in the final dry film coating than when the hydrophobic substance is in a dissolved state and precipitates from the dissolved state, the more so because less controllable evaporation conditions prevail during pan coating as described in Brophy & Deasy (1981).

The film-forming polymeric substances contemplated for the purpose of the present invention are pharmaceutically acceptable film-forming polymers which are substantially water-soluble, but which permit water diffusion. Examples of such substances are cellulose derivatives, for instance ethylcellulose, acrylic polymers, vinyl polymers, and other high molecular synthetic polymers such as ethylcellulose, cellulose acetate, cellulose propionate, cellulose butyrate, cellulose valerate, cellulose acetate propionate, polyvinyl acetate, polyvinyl formal, polyvinyl butyral, ladder polymer of sesquiphenyl siloxane, polymethyl methacrylate, polycarbonate, polystyrene, polyester, coumaroneindene polymer, polybutadiene, vinyl chloride-vinyl acetate copolymer, ethylene-vinyl acetate copolymer and vinyl chloride-propylene-vinyl acetate copolymer.

The hydrophobic substance incorporated according to the invention may be any pharmaceutically acceptable hydrophobic substance which will result in the desired retardation of the diffusion (in the present context, the term "hydrophobic" indicates substances which, relative to water, have a contact angle of more than 90°). All such hydrophobic substances are substances which, by themselves, that is, without admixture with other components, are capable of forming a continuous phase (that is, either by being molten or by being dissolved and subjected to removal of the solvent). The amount of the hydrophobic substance incorporated will depend on the properties of the hydrophobic substance, in particular its hydrophobicity, with respect to delaying the water diffusion of the polymeric film.

Typical examples of such hydrophobic substances are substances selected from hydrocarbons and hydrocarbon derivatives, waxes, oils and fats, and mixtures thereof.

One class of hydrophobic substances which are interesting for the purpose of the present invention are wax-like substances. Examples of wax-like substances are beef tallow, whale wax, beeswax, solid paraffin, castor wax, and higher fatty acids such as myristic, palmitic, stearic and behenic acids and esters thereof.

The hydrophobic substances will usually have a melting temperature below 100° C.

The hydrophobic substance, e.g. a waxy substance such as paraffin wax, will normally be present in the coating in an amount of between about 1 and 25%, in particular between 3 and 20%, especially between about 5 and 18%, such as between about 9 and about 17%, calculated on the weight of the dry matter of the coating suspension.

The individual units of the multiple-units formulations according to the invention will normally be either coated crystals or pellets (coated cores). In the pellets, the core is constituted by a combination of active substance and excipients. A type of core which is widely used in the known art (vide, e.g., Eur. Patent Application No. 79850 110) is a substantially spherical particle of a size of about 0.5–1 mm consisting of excipient(s) with active substance applied to its surface. Typical cores of this type are the so-called "non-pareil" cores where the excipients are in the form of spherical particles of saccharose. It is also known, e.g., from GB Patent Specification No. 1 468 172, to prepare cores which are cross-sectionally substantially homogeneous. In the present context, the term "cores which are cross-sectionally substantially homogeneous" designates cores in which the active substance is not confined to an exterior layer on the core body, in other words normally cores which, through the cross-section of the core body, contain substantially the same type of composition comprising microparticles containing active substance, in contrast to the non-pareil type of cores which each consist of an excipient body with active substance applied to its surface, and in contrast to coated crystal units which are substantially monolithic crystals. From this definition, it will be understood that the cores which are cross-sectionally substantially homogeneous will normally consist of a mixture of active substance with excipient(s), (and in spite of the term "homogeneous", this mixture will not necessarily be qualitatively or quantitatively homogeneous through the cross-section of the particle but may show, e.g., a concentration gradient of one or more of its constituents) or they may consist substantially solely of active substance in a non-monolithic form, e.g. as a sintered mass of crystalline or amorphous particles of active substance. In the following specification and claims, such cores which are cross-sectionally substantially homogeneous will, for the sake of brevity, often simply be designated "cores".

According to a particular aspect of the invention, diffusion-coated cores containing a medicament substance which has a pH-dependent solubility comprise a buffer substance which, in accordance with the principles disclosed in GB Pat. No. 1 468 172, serves to establish a controlled pH interval inside the pellets during passage of the pellets through the gastrointestinal system, thereby securing that the medicament substance in the cores will be dissolved under controlled pH conditions.

The pharmaceutical oral controlled release multiple-units formulation according to the invention will typically be a capsule containing a multiplicity of the units, typically more than 100, a sachet containing a multiplicity of the units, typically more than 1000, or a tablet made from a multiplicity of the units, typically more than 100, in such a manner that the tablet will disintegrate substantially immediately upon ingestion in the stomach into a multiplicity of individual units which are distributed freely throughout the gastro-intestinal tract.

The formulations mentioned above may be prepared by conventional methods known in the pharmaceutical industry. One particularly interesting shape of a tablet according to the invention, in particular when the tablet is to contain a rather large amount of active substance and is to be easy to swallow, is a shape substantially corresponding to a cylinder with rounded ends, a raised area circumscribing the periphery of the cylinder in the form of flat belt and a score dividing the cylinder, but not the peripheral belt, into two parts, substantially as shown in the drawing. As an example of such tablets may be mentioned tablets in which the active substance is potassium chloride crystals, e.g. in tablet sizes comprising 600 mg and 750 mg of potassium chloride, respectively, for use as potassium supplement for patients in diuretic treatment.

DETAILED DESCRIPTION OF INVENTION

Cores

Figure 1:
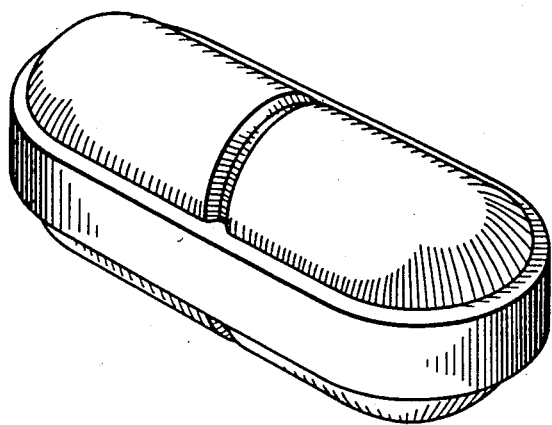
FIGS. 1 and 2 illustrate examples of the divisible tablets according to the invention.

According to the invention, the cores are preferably cross-sectionally substantially homogeneous cores. The use of cross-sectionally substantially homogeneous cores offers several advantages.

Firstly, it is easy to produce cross-sectionally substantially homogeneous cores reproducibly on a large scale, for instance by means of automatic equipment, because the components therefor are normally simply mixed in the prescribed proportions, which means that intercore variations in composition, e.g., concentration of active substance, can be kept within narrow limits. Secondly, the concentration of active substance in the core can be varied within very wide limits (generally between 1 and 90% by weight), which renders it possible to optimize the concentration of active substance in the single core in order to minimize capsule sizes for a given dosage strength and thereby optimize patient compliance. Thirdly, the size of the cores may be easily adjusted as desired, to improve the distribution pattern of the units throughout the gastrointestinal tract; this forms a contrast to the non-pareil technique where the size variation is limited by the available standard sizes. Fourthly, the composition of the cores may be optimized with respect to the extent of drug availability, i.e., to enhance the release of the active substance.

The cores are typically made by granulating particles of the active substance together with excipients, including bulk agents such as carbohydrates and derivatives thereof such as starch and starch derivatives, including microcrystalline cellulose, binders such as cellulose derivatives, including methylcellulose or hydroxypropylmethylcellulose, polyethylene glycol, polyvinylpyrrolidone, agar, or gelatin, for instance by treatment in a high speed mixer (to directly obtain compact-shaped cores), or by treatment in a planet mixer with subsequent extrusion of the mixture into strings of a predetermined diameter approaching the desired final cross-sectional dimension of the cores and treatment of the strings in a marumerizer or similar equipment to obtain compact-shaped cores. The diameter of the cores is normally adapted so that the diameter of the coated core is about 0.4–1.2 mm, in particular about 0.5–1.0 mm, especially about 0.5–0.8 mm, such as 0.5–0.7 mm. A preferred diameter of the coated cores is about 0.5–0.6 mm.

In accordance with a particular aspect of the invention, the predetermined controlled release of the active substance may be changed by changing the density of the cores, and thus, the time of arrival of the cores in the predetermined section of the intestine may be varied at will. By increasing the density of the cores with resulting increased transit time of the coated cores (Bechgaard & Ladefoged, 1978), a more delayed and longer lasting absorption phase is obtained, that is, a longer period during which the absorption of the active substance takes place after the substance has been released by diffusion of the coating, thus having become available for absorption.

Examples of excipients which may be used to increase the density of the cores are described in U.S. Pat. No. 4,193,985 and include heavy particulate substances such as barium sulphate, titanium oxide, zinc oxides, and iron salts.

According to another particular aspect of the invention, a buffer substance is incorporated in the core when the medicament substance is one which has a pH-dependent solubility. The buffer or buffer mixture is preferably so selected that the buffered system in the cores obtains a pH between 1 and 7.5, in particular a pH in the range from about 4 to about 6. The amount of buffer should be sufficient to obtain a buffer effect during the period necessary for the release of the active substance and may easily be determined by the skilled art worker through simple tests. As examples of suitable pharmaceutically acceptable buffer substances may be mentioned primary, secondary or tertiary salts of phosphoric acid or salts of phthalic acid, citric acid, tartaric acid, or salts of aminoacids such as glycine, or mixtures of such buffer salts. A typical concentration of buffer substance in the cores is in the range of from about 3 to about 40% by weight, calculated on the core constituents, preferably from about 5 to about 30% by weight.

Crystals

When the units coated according to the invention are crystals, they normally have a size between about 0.2 and 1.5 mm, preferably between about 0.2 and 0.6 mm. As an important example of an active substance which is suitably used in the form of crystals, potassium chloride may be mentioned.

Active Substance

The active substance in the formulations according to the invention may be any active substance which is advantageously administered in a controlled release multiple-units formulation. Examples of suitable active substances are found among almost all therapeutic groups, including diuretics, antiepileptics, sedatives, antiarrhytmics, antirheumatics, β-blockers, vasodilators, analgesics, bronchodilators, hormones, oral antidiabetics, antihypertensives, antiinflammatorics, and antidepressives.

Among these active substances, some are characterized as having a pH-dependent solubility, others as having a pH-independent solubility.

As examples of active substances which have a pH-dependent solubility (that is, a solubility which differs corresponding to a ratio of $10:10^3$ over the physiological pH range of 1–7.5) may be mentioned pindolol, quinidine salts, lithium carbonate, acemetacin, vincamine, dipyridamol, theophyllin, dextropropoxyphen, amitriptylin, and hydralazin. Active substances having a pH-dependent solubility are preferably incorporated in cores in combination with buffer substances such as discussed above, in order to obtain a dissolution of active substance which is substantially independent of the gastrointestinal pH variations through which the units pass.

As examples of active substances with a solubility which is not pH-dependent may be mentioned atenolol.

Especially important formulations according to the invention are formulations in which the active substance, apart from being a substance about which it is known or indicated from a pharmacokinetic and/or clinical point of view that it is advantageously administered in a controlled release multiple-units formulation, is a substance which exerts an irritating effect on the gastric mucosa such as acetylsalicylic acid, potassium chloride, and lithium salts.

In utilizing the principle of the invention, the units are freely distributed throughout the gastrointestinal tract, independent of gastric emptying, as the units are small enough to pass the pylorus even when the sphincter is contracted. This makes it possible to obtain a low concentration at the mucosa and thus to minimize the risk of local irritation.

Coating

The diffusion-coating applied on the units according to the invention is applied from a solution and/or suspension in an organic solvent. As examples of suitable solvents may be mentioned alcohols such as ethanol, methanol, isopropanol, and propanol, ketones such as acetone, and toluene. The application of the coating is performed in a fluidized bed.

Examples of diffusion-coating materials which may be used for the purpose of the present invention are mentioned above. Preferred coating materials are cellulose derivatives such as, e.g., ethylcellulose, and acrylic polymers such as polymethylmethacrylate, e.g., the so-called Eudragit ® coatings.

The coating material may be admixed with various excipients such as plasticizers, inert fillers, and pigments, in a manner known per se.

Examples of plasticizers include triacetin, Myvacet TM 9-40T (acetylated monoglyceride), rape oil, olive oil, sesame oil, acetyltributylcitrate, acetyltriethylcitrate, glycerin, sorbitol, diethyloxalate, diethylmalate, diethylfumarate, diethylsuccinate, diethylmalonate, diethyltartrate, tri-n-butylcitrate, dibutylphthalate, diethylphthalate, dioctylphthalate, dibutylsebacate, triethylcitrate, tributylcitrate, glyceroltributyrate, polyethyleneglycol, propyleneglycol, and mixtures of the above. The plasticizer is normally incorporated in an amount of less than 1% by weight, calculated on the dry matter content of the coating mixture.

The amount of coating applied is adapted so as to obtain a predetermined dissolution characteristic of the coated units. Normally, the amount of the coating will be about 0.5–25% by weight, calculated as dry matter on the total weight of the units, typically about 1–10% by weight, depending on the predetermined dissolution characteristics of the active substance and the desired release profile.

The diffusion coating applied on the units according to the invention may also be a diffusion coating which is applied from a solution and/or suspension in water. The application of the coating is typically performed in a fluidized bed or by pan coating.

Examples of such water-based diffusion coating materials which may be used for the purpose of the present invention are coatings selected from the group consisting of acrylic polymers and copolymers, e.g., a polymerisate of acrylic acid ethyl ethers and methacrylic acid methyl ester such as Eudragit ®E30D or ethylcellulose such as Aquacoat ®ECD-30. The coating material may be admixed with various excipients such as plasticizers, inert fillers, and pigments, in a manner known per se. Examples of plasticizers are the same as mentioned in connection with the organic solvent-based coating mixtures. The amount of coating applied from a water-based coating mixture is adapted so as to obtain a predetermined dissolution characteristic of the coated units. Normally, the amount of the coating will be about 2–25% by weight, calculated as dry matter on the total weight of the units, typically about 15% by weight, depending on the predetermined dissolution characteristics of the active substance and the desired release profile.

Dosage forms

The units prepared according to the invention may be incorporated in normal pharmaceutical dosage forms or formulations such as capsules containing a multiplicity of the units, sachets containing a multiplicity of the units, or tablets which will disintegrate substantially immediately upon ingestion in the stomach to form a multiplicity of individual units.

The adjuvants and excipients used in the preparation of disintegratable tablets are of the same kind as conventionally used in the pharmaceutical industry for this purpose. Examples of filler or diluents useful for preparing tablets according to the invention are lactose, sucrose, dextrose, mannitol, calcium sulphate, dicalcium phosphate, tricalcium phosphate, starches such as rice starch and microcrystalline cellulose. Useful binders are acacia, tragacanth, gelatine, sucrose, pregelatinized starch, starch, sodium alginate, ammonium calcium alginate, methylcellulose, sodium carboxymethylcellulose, ethylcellulose, hydroxypropylmethylcellulose, polyvinylpyrrolidone, magnesium aluminum silicate, and polyacrylamides. As examples of disintegrants may be mentioned starches and starch derivatives, clays, and celluloses including microcrystalline cellulose, alginates and gums, including agar, and tragacanth. As "lubricants", "gliders" and "anti-adherents" may be mentioned metallic stearates, talc, high melting point waxes, and colloidal silicon dioxide.

When it is desired to use excipients or adjuvants for the preparation of sachets or capsules, such as fillers and lubricants, these may be of the same type as described above. The filling of capsules and sachets and the compression of tablets are performed by manners known per se.

MATERIALS AND METHODS

Potassium chloride:
Ph.Eur. fraction, 0.2–0.6 mm.

Isopropanol:
BP 80
Paraffin:
NF XV
Acetyl tributyl citrate:
Citroflex ®A4; supplied by Pfizer A/S, Copenhagen, Denmark.
Ethylcellulose:
NF XV
Colloidal silicon dioxide:
USP XX
Magnesium stearate:
Ph.Eur.
Microcrystalline cellulose:
BPC 79
Rice starch:
Ph.Eur.
Talc:
Ph.Eur.

Uniformity of Mass

The uniformity of mass was determined according to Ph. Eur. 2nd Ed. 1, V.5.2.

Disintegration Time of Tablets

The disintegration time of tablets was measured according to Ph.Eur. 2nd Ed.1, V.5.1.1. using a disc.

Assay for Potassium Chloride

The content of potassium chloride was determined by heating 10 tablets in water until boiling.

After cooling and filtration, the filtrate was titrated with 0.1N silver nitrate, using dichlorofluorescein as the indicator.

Determination of in Vitro Dissolution Rate of Tablets

In vitro dissolution rates were determined according to Baggesen et al. (1981). The rotation speed was 30±1 r.p.m., and the dissolution medium was 25 ml of 0.1M hydrochloric acid (pH 1.2), maintained at 37°±0.1° C. Release of potassium chloride into the dissolution medium was measured by means of an ion-selective electrode.

Determination of Potassium in Urine

Potassium in urine was measured by a flame photometric method.

EXAMPLE 1

Preparation of Film-coated Potassium Chloride Crystals

Preparation of Film-coating Mixture

A film-coating mixture was prepared from 1.600 kg paraffin, 0.560 kg acetyl tributyl citrate, 10.500 kg ethylcellulose, 0.160 kg silicium dioxide and 212.180 kg isopropanol.

The paraffin was melted in 70 kg of the isopropanol by heating in a mixer equipped with a heating jacket at 70° C. The acetyl tributyl citrate, the ethylcellulose and the silicium dioxide were added under vigorous stirring. The vigorous stirring was continued for about 1 hour, whereupon isopropanol was added up to 225 kg, and the stirring speed was reduced. The film-coating mixture was then homogeneous and ready for use.

The film-coating mixture is used warm at approximately 70° C.

Application of Film-coating on Potassium Chloride Crystals

The film-coating mixture prepared as described above was sprayed onto 150 kg potassium chloride crystals using a fluidized bed. The potassium chloride crystals were fluidized, and the film-coating mixture was sprayed onto the crystals using an outlet air temperature of about 60° C. at a rate of about 500 g of film-coating mixture/minute. After the application of the film-coating mixture, the film-coated crystals were dried in a fluidized bed for 20 minutes, whereupon the film-coated crystals were cooled to about 20° C., while still lying in the fluidized bed.

The film-coated crystals prepared as described above may be used immediately for the preparation of tablets, capsules or sachets or may be stored for later use.

EXAMPLE 2

Preparation of Tablets Containing 750 mg Potassium Chloride (10 mmol.)

Tablets were prepared from 33.0 kg talc, 825.0 kg film-coated potassium chloride crystals (film-coated as described in Example 1), 30.0 kg microcrystalline cellulose, 282.0 kg rice starch and 30.0 kg of a 1:9 mixture of magnesium stearate and talc.

The talc was mixed with the film-coated potassium chloride crystals in a 2000 liter cube blender for 10 minutes.

The microcrystalline cellulose and the rice starch were added, and the components were mixed for 10 minutes. The 1:9 mixture of magnesium stearate and talc was mixed with a portion of about 30 kg of the resulting mixture for 5 minutes and was then added to the main portion of the mixture and mixed for 5 minutes.

The resulting mixture was compressed into tablets having a weight of 1200 mg, each comprising 750 mg potassium chloride. The tablets were compressed by using an oval punch and a pressure of 2200 kg on a conventional rotating tabletting machine.

Characteristics of the Tablets

Disintegration time (determined as described under MATERIALS AND METHODS): Approximately 60 seconds This disintegration time is well within the official requirements of a disintegration of less than 15 minutes when tested by this method.

Uniformity of mass (determined as described under MATERIALS AND METHODS):

| | |
|---|---|
| Mean = | 1192 mg |
| Standard deviaton = | 13.3 mg |
| Relative variation = in % | 1.12 |
| min. = | 1157 mg |
| max. = | 1210 mg |

The uniformity of mass is well within the official requirements permitting a variation from 1132 to 1252 mg per tablet.

In Vitro Dissolution Rate:

| Time | Potassium Chloride: | |
|---|---|---|
| | Mean (mg) | Standard Deviation (mg) |
| 1 h | 220 | 8.4 |
| 2 h | 336 | 9.2 |
| 6 h | 588 | 7.8 |

Assay for Potassium Chloride: 745 mg/tablet of mean weight.

EXAMPLE 3

Investigation of the effect of hydrophobic substance

Preparation of coating suspension

Three portions of coating suspension with varying amounts of paraffin were prepaed as described in Example 1 from the following amounts of paraffin, acetyl tributyl citrate, ethylcellulose, silicium dioxide and isopropanol, respectively:

| Type of coating suspension: | A | B | C |
|---|---|---|---|
| Percent of paraffin: | 0 | 0.35 | 0.7 |
| Amount of paraffin, kg | 0 | 0.033 | 0.062 |
| acety tributyl citrate, kg | 0.025 | 0.025 | 0.025 |
| ethycellulose, kg | 0.467 | 0.437 | 0.410 |
| silicium dioxide, kg | 0.008 | 0.007 | 0.007 |
| isopropanol, kg | 9.500 | 9.498 | 9.496 |

The coating suspensions obtained were sprayed onto three portions of potassium chloride crystals of 5 kg using a fluidized bed under the same process conditions as described in Example 1.

From the three portions of film-coated potassium chloride crystals, tablets containing 750 mg potassium chloride were prepared as described in Example 2.

The in vitro dissolution rate of potassium chloride after 1 hour was measured for all 3 batches of crystals and tablets, resp. and the following results were obtained (n=6):

TABLE 1

Percentage of Potassium of Released within 1 hour. Mean (S.D.), %

| Type of coating susp. | A | B | C |
|---|---|---|---|
| [1]Amount of paraffn, % | 0 | 0.35 | 0.7 |
| Film-coated crystass | 56.3 | 50.8 | 20.2 |
| | (2.3) | (6.4) | (1.8) |
| [2]Tablets | 71.1 | 61.7 | 31.7 |
| | (4.6) | (1.7) | (1.3) |

[1]in the coating suspensions.
[2]percent released calculated on 750 mg potassium chloride per tablet.

Figure 3:
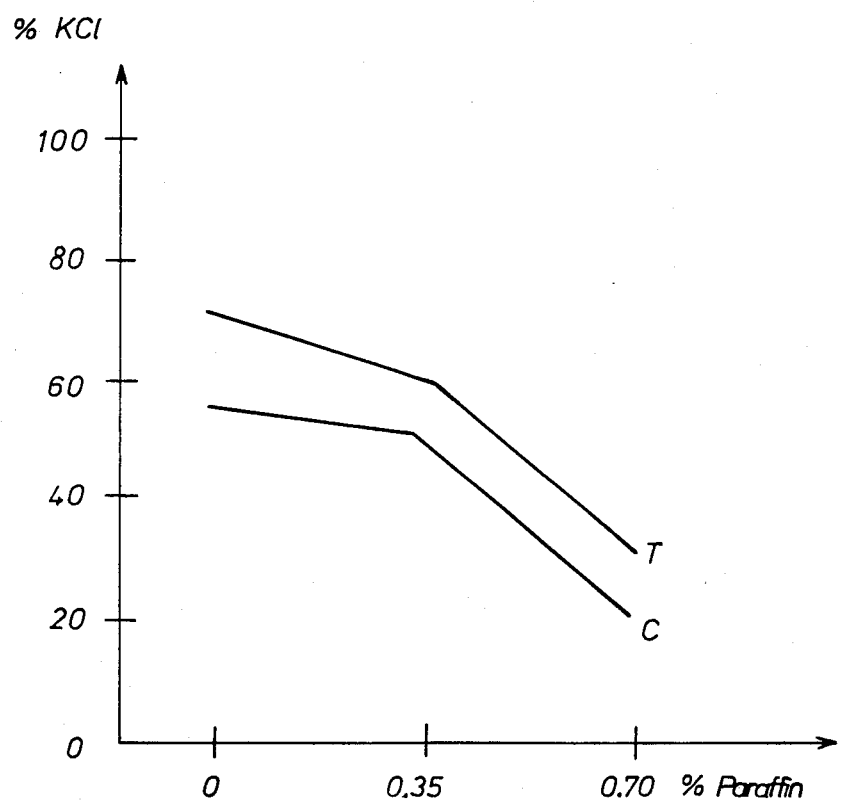
FIG. 3 graphically shows the in vitro dissolution rate of potassium chloride from crystals (C) and tablets (T).

The results are shown graphically, vide FIG. 3. There is a minor increase in dissolution rate due to the mixing of film-coated crystals with the adjuvants and compression of tablets. But first of all, the results illustrate the fact that the recommended amount of paraffin (0.7%), used in Example 1, will give the most effective diffusion resistance of the coating towards potassium. To increase the amount of paraffin further results in processability-problems as to nozzle blocking and is therefore not possible.

EXAMPLE 4

Preparation of Tablets Containing 600 mg Potassium Chloride (8 mmol.)

Figure 2:
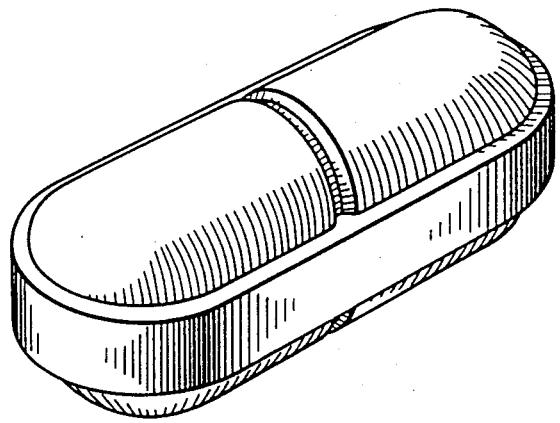

Tablets having a weight of 960 mg, each comprising 600 mg potassium chloride were compressed from a mixture prepared as described in Example 2. The tablets were compressed using a capsule-shaped punch on a conventional rotating tabletting machine, to obtain tablets of the shape shown in FIGS. 1 and 2.

Characteristics of the Tablets

Disintegration time (determined as described under MATERIALS AND METHODS): 65–80 seconds This disintegration time is well within the official requirements of a disintegration of less than 15 minutes when tested by this method.

Uniformity of mass (determined as described under MATERIALS AND METHODS):

| Mean = | 955 mg |
|---|---|
| Standard deviation = | 5.67 mg |
| Relative variation = in % | 0.59 |
| min. = | 945 mg |
| max. = | 964 mg |

The uniformity of mass is well within the official requirements permitting a variation from 907 to 1003 mg per tablet.

In Vitro Dissolution Rate:

| Time | Potassium chloride: | |
|---|---|---|
| | Mean (mg) | Standard Deviation (mg) |
| 1 h | 159 | 6.8 |
| 2 h | 231 | 11.8 |
| 6 h | 427 | 9.1 |

Assay for Potassium Chloride: 606 mg/tablet.

EXAMPLE 5

Bioavailability of Potassium from Controlled-Release Multiple-Units and Single-Unit Tablets With and Without Water Loading Subjects 13 healthy volunteers, 8 females and 5 males, aged 20–51 years (median 41 years) and weighing 55–88 kg (median 66 kg), participated in the two studies, after giving informed consent.

Drug formulation

Controlled release potassium chloride products were administered in the form of potassium chloride tablets, 8 mmol, prepared as described in Example 4, and Slow-K, 8 mmol (Ciba) as a reference; they show complete release in vitro of their potassium content within 8–10 hours and 2–4 hours, respectively.

Experimental design

The tablets were tested in two studies both of which were carried out in a randomised triple crossover design.

The subjects were given diets of about 2000 kilocalories daily, all providing less than 30 mmol of potassium.

Study 1: Single Dose Study: 6 Subjects with Water Loading

The study consisted of three 3-day observation periods in three consecutive weeks. Each subject received an individual diet, identical on all nine observation days.

In this way a different diet could be given to each subject.

On Day 1 the low potassium diet was introduced.

On Day 2 (baseline day) a water loading regimen was established; the subjects were required to take 100 ml water every hour from 09:00 h to 20:00 h inclusive, total 1200 ml. All urine was collected from 09:00 h until 09:00 h on Day 3, and was divided into two fractions, 09:00 to 21:00 h and 21:00 to 09:00 h on Day 3.

On Day 3 a single oral dose of potassium of 32 mmol (4 tablets) was administered at 09:00 h, after the bladder had been emptied. Water loading and collection of urine was performed as on Day 2.

Study 2: Single Dose Study: 7 Subjects without Water Loading

In contrast to Study 1, a 4-day observation period was used. The subjects received a diet of their own choice; thus, the diet could differ from day to day and vary between subjects.

From Day 1 onwards, the low potassium diet was taken. On Day 3 all urine was collected in fractions according to the procedure described in Study 1, Day 2. No water load was introduced. On Day 4 a single oral dose of 32 mmol of potassium (4 tablets) was administered, and urine collection was continued as on Day 3.

Chemical Analysis

Urine potassium was determined by means of an IL 543 flame photometer. The coefficient of variation of analyses was less than 4%.

TABLE 2

Study 1
Increase in urinary potassium excretion, ΔK (mmol)

| Fraction Treatm. | 0–12 h Slow-K | 0–12 h Invention | 12–24 h Slow-K | 12–24 h Invention | 0–24 h Slow-K | 0–24 h Invention | $\frac{\text{Invention}}{\text{Slow-K}} \times 100$ |
|---|---|---|---|---|---|---|---|
| Subject |  |  |  |  |  |  |  |
| 1 | 2.92 | 10.73 | 10.96 | 6.27 | 13.88 | 17.00 | 123 |
| 2 | 8.74 | 18.56 | 5.60 | −1.37 | 14.34 | 17.19 | 120 |
| 3 | 6.64 | 17.99 | 7.84 | −2.04 | 14.48 | 15.95 | 110 |
| 4 | 9.41 | 0.12 | 8.00 | 15.54 | 17.41 | 15.66 | 90 |
| 5 | 9.40 | 9.37 | 6.39 | 6.51 | 15.79 | 15.88 | 101 |
| 6 | 8.66 | 13.95 | 7.85 | 1.84 | 16.51 | 15.79 | 96 |
| Median | 8.70 | 12.34 | 7.85 | 4.06 | 15.14 | 15.92 | 109 |
| Average | 7.63 | 11.79 | 7.77 | 4.46 | 15.40 | 16.25 | 107 |
| SD | 2.52 | 6.81 | 1.84 | 6.53 | 1.39 | 0.67 | — |

TABLE 3

Study 2:
Increase in urinary potassium excretion, ΔK (mmol)

| Fraction Treatm. | 0–12 h Slow-K | 0–12 h Invention | 12–24 h Slow-K | 12–24 h Invention | 0–24 h Slow-K | 0–24 h Invention | $\frac{\text{Invention}}{\text{Slow-K}} \times 100$ |
|---|---|---|---|---|---|---|---|
| Subject |  |  |  |  |  |  |  |
| 1 | 10.88 | 10.66 | 3.28 | 6.44 | 14.16 | 17.10 | 121 |
| 2 | 25.35 | 6.20 | 0.88 | 2.91 | 26.23 | 9.11 | 35 |
| 3 | 4.07 | 9.99 | 6.46 | 2.28 | 10.53 | 12.27 | 117 |
| 4 | 8.46 | 29.43 | 4.18 | 6.40 | 12.64 | 35.83 | 283 |
| 5 | 7.16 | 4.48 | −6.20 | 7.83 | 0.96 | 12.31 | 1282 |
| 6 | 23.49 | 15.35 | 0.85 | −0.26 | 24.34 | 15.09 | 62 |
| 7 | 20.72 | 13.66 | 4.64 | −5.65 | 25.36 | 8.01 | 32 |
| Median | 10.88 | 10.66 | 3.28 | 2.91 | 14.16 | 12.31 | 117 |
| Average | 14.30 | 12.82 | 2.01 | 2.85 | 16.32 | 15.67 | 276 |
| SD | 8.65 | 8.26 | 4.14 | 4.70 | 9.42 | 9.43 | — |

TABLE 4

Statistical analysis of the data presented in Tables 2 and 3

| Fraction Treatm. | 0–12 h Slow-K | 0–12 h Invention | 12–24 h Slow-K | 12–24 h Invention | 0–24 h Slow-K | 0–24 h Invention | $\frac{\text{Invention}}{\text{Slow-K}} \times 100$ |
|---|---|---|---|---|---|---|---|
| Study |  |  |  |  |  |  |  |
| 1 Median[1] |  |  | 7.93 |  |  | 15.73 | 110 |
| 2 | 10.77 |  |  | 2.78 |  |  |  |
| 1 Average[1] |  |  | 7.92 |  |  | 15.92 | 198 |
| 2 | 13.56 |  |  | 2.43 |  |  |  |

[1] Only statistically significant (5% level) values given.

Irrespective of differences in the methods employed in the two availability studies, either with or without water loading, the extent of availability of the tablet according to the invention and of Slow-K were found to be equivalent, (Table 4). The median relative bioavailability of the tablet of the invention was 109 and 117% in Studies 1 and 2, respectively.

The increase in potassium excretion during the 24 h period after drug administration was about 50% (16 mmol) of the ingested dosage. This observation is in accordance with other studies (Bechgaard et al. 1979; Ben-Ishay and Engelman 1973) using the same very low dietary potassium intake (less than 30 mmol), and it suggests that some intracellular potassium depots may be depleted during the pre-treatment period, but begin to be restored on the day of treatment. Other studies (Tannen and Cordano 1978; Skoutakis et al. 1979) indicate, however, that a higher percentage of a dose might be recovered if the dietary potassium intake were only limited to 60 or 70 mmol.

LITERATURE

G.B. Pat. No. 1,468,172

Eur. Patent Application No. 79 850 110, Publication 0 013 262

U.S. Pat. No. 4,193,985

Bechgaard, H. Hegermann Nielsen, G & Aggerback, A (1979) Kalinorm. En polydepot tablet med kontrolleretøudlsning af kaliumklorid. In vitro og in vivo dokumentation. Farm. Tid. 89; 761-766.

Ben-Ishay, D, Englemann, K (1979) Bioavailability of Potassium from a Slow-Release Tablet. Clin. Pharmacol. Ther. 14: 250-258.

Stoutakis, V. A., Acchiardo, S. R. Feigenbaum, A. S. (1979) Bioavailability of Potassium from a Slow-Release Tablet. Curr. Ther. Res. 25: 104–112.

Tannen, R. L., Cordano, A (1978) Pharmakokinetics and Effects on Fecal Blood Loss of a Controlled Release Potassium Chloride Tablet, J. Pharmacol. Exp. Therm.: 240-246.

Brophy, M. R. & Deary, P. B., Influence of coating and core modifications on the in vitro release of methylene blue from ethylcellulose microcapsules produced by pan coating procedure. J. Pharmacol, 33 (1981) 495-99

Harris, M. S., Preparation and Release Characteristics of potassium chloride microcapsules. J. Pharm, 70 (1981) 391-94

Baggensen S, Bechgaard H, & Schmidt K (1981) Content and dissolution uniformity testing of controlled-release products: The Repro-Dose ® quality control procedure. Pharm. Acta Helv 56, 85–92

Bechgaard, H & Hegermann Nielsen, G (1978) Controlled release multiple-units and single-units doses. A literature review. Drug Develop Ind Pharm 4, 53–67.

Bechgaard, H & Ladefoged, K (1978) Distribution of pellets in the gastrointestinal tract. The influence on transit time exerted by the density or diameter of pellets. J. Pharm Pharmacol 30, 690-692.

Bechgaard, H & Baggesen, S (1980) Propoxyphene and norpropoxyphene: Influence of type of controlled release formulation on intra- and intersubject variations. J Pharm Sci 69, 1237-1330.

Bogentoft, C, Carlsson, I, Ekenved, G & Magnusson, A (1978) Influence of food on the absorption of acetylsalicylic acid from enteric-coated dosage forms. Eur J Clin Pharmacol 14, 351–355.

Green, DM (1966) Tablets of coated aspirin microspherules—A new dosage form. J New Drugs 6, 294–303.

McDonald, PJ, Mather, LE & Story, MJ (1977) Studies on absorption of a newly developed enteric-coated erythromycin base. J Clin Pharmacol 17, 601–606.

Snedecor, GW & Cochran, WG (1967) Statistical Methods. Iowa State University Press, Iowa, 271–275.

We claim:

1. A method for preparing a pharmaceutical oral controlled release composition in which individual units comprise coated units of an active substance which is subject to controlled release as a result of coating the units with a substantially water-insoluble, but water-diffusable controlled release coating, comprising applying, on units comprising the active substance, a film-coating mixture comprising a solvent, a film-forming substance dissolved in the solvent, and a hydrophobic substance substantially microdispersed in the film-coating mixture in a molten, but undissolved state, the film-coating mixture being applied at a temperature above the melting point of the hydrophobic substance.

2. A method according to claim 1, wherein the film-coating mixture is applied at a temperature of about 70° C.

3. A method according to claim 1, wherein the hydrophobic substance is present in an amount of between about 1 and 25%, calculated on the weight of the dry matter of the coating suspension.

4. A method according to claim 3, wherein the hydrophobic substance is present in an amount of between about 3 and 20%, calculated on the weight of the dry matter of the coating suspension.

5. A method according to claim 1, wherein the film-forming substance is selected from ethylcellulose, cellulose acetate, cellulose propionate, cellulose butyrate, cellulose valerate, cellulose acetate propionate, polyvinyl acetate, polyvinyl formal, polyvinyl butyral, ladder polymer of sesquiphenyl siloxane, polymethyl methacrylate, polycarbonate, polystyrene, polyester, coumarone-indene polymer, polybutadiene, vinyl chloride-vinyl acetate copolymer, ethylene-vinyl acetate copolymer and vinyl chloride-propylene-vinyl acetate copolymer.

6. A method according to claim 1, wherein the hydrophobic substance is selected from hydrocarbons and hydrocarbon derivatives, waxes, oils and fats, and mixtures thereof.

7. A method according to claim 6, wherein the hydrophobic substance is a wax-like substance selected from beef tallow, whale wax, bees-wax, paraffin wax, and castor wax, and myristic, palmitic, stearic and behenic acids and esters thereof.

8. A method according to claim 1, wherein the film-coating mixture contains a plasticizer selected from triacetin, acetylated monoglyceride, rape oil, olive oil, sesame oil, acetyltributylcitrate, acetyltriethylcitrate, glycerin, sorbitol, diethyloxalate, diethylmalate, diethylfumarate, diethylsuccinate, diethylmalonate, dioctylphthalate, dibutylsebacate, triethylcitrate, tributylcitrate, glyceroltributyrate, polyethyleneglycol, propyleneglycol, and mixtures of the above.

9. A method according to clam 1, wherein the active substance in the units is potassium chloride.

10. A method according to claim 9, wherein the potassium chloride is in the form of potassium chloride crystals, each unit substantially comprising one crystal.

11. A method according to claim 1 in which the coated units are of a size between about 0.5 and 1.5 mm.

12. A method according to claim 11, wherein the coated units are of a size between 0.2 and 0.6 mm.

13. A method according to claim 1, wherein a multiplicity of the units is combined into a multiple-units formulation which is either a capsule, or a tablet which disintegrates substantially immediately upon ingestion in the stomach into a multiplicity of individual units, or a sachet.

14. A method according to claim 13 in which the active substance is potassium chloride in the form of crystals.

15. A method according to claim 13, wherein a multiplicity of the units is combined into a tablet which is shaped substantially as a cylinder with rounded ends, a raised area circumscribing the periphery of the cylinder in the form of a flat belt and a score dividing the cylinder, but not the peripheral belt, into two parts.

16. A method according to claim 15, wherein the tablet is made to contain about 600 mg of potassium chloride.

17. A method according to claim 15, wherein the tablet is made to contain about 750 mg of potassium chloride.

18. A method according to claim 1, wherein the hydrophobic substance is present in an amount of between about 5 and 18%, calculated on the weight of the dry matter of the coating suspension.

19. A method according to claim 18, wherein the hydrophobic substance is present in an amount of between about 9 and 17%, calculated on the weight of the dry matter of the coating suspension.

20. A method for preparing a pharmaceutical oral controlled release composition in which individual units comprise coated units of an active substance comprising potassium chloride which is subject to controlled release as a result of coating the units with a substantially water-insoluble, but water diffusable controlled release coating, comprising: applying, on units comprising the active substance, a film-coating mixture comprising solvent, a film-forming substance dissolved in the solvent, the film-forming substance comprising ethyl cellulose, and a hydrophobic substance substantially microdispersed in the film-coating mixture in a molten, but undissolved state, the film-coating mixture being applied at a temperature above the melting point of the hydrophobic substance.

* * * * *